US006404848B1

United States Patent
Ishisaka et al.

(10) Patent No.: US 6,404,848 B1
(45) Date of Patent: Jun. 11, 2002

(54) X-RAY IMAGE RADIOGRAPHING METHOD AND X-RAY IMAGE RADIOGRAPHING APPARATUS

(75) Inventors: Akira Ishisaka; Chika Honda; Hiromu Ohara, all of Hino (JP)

(73) Assignee: Konica Corporation (JP)

( * ) Notice: Subject to any disclaimer, the term of this patent is extended or adjusted under 35 U.S.C. 154(b) by 0 days.

(21) Appl. No.: 09/667,009

(22) Filed: Sep. 21, 2000

(30) Foreign Application Priority Data

Sep. 21, 1999 (JP) .......................................... 11-266604
Feb. 22, 2000 (JP) ...................................... 2000-044381

(51) Int. Cl.[7] .............................................. G01N 23/04
(52) U.S. Cl. .......................................... 378/62; 378/70
(58) Field of Search ...................................... 378/62, 70

(56) References Cited

FOREIGN PATENT DOCUMENTS

| EP | 0 050 510 A | 4/1982 |
| EP | 0 220 501 A | 5/1987 |
| WO | WO 96 31098 | 10/1996 |

OTHER PUBLICATIONS

Umetani Keiji, et al., "X–ray refraction contrast imaging using synchroton radiation at spring–8", Proceedings of the 1999 Medical Imaging Physics of Medical Imaging, Feb. 21–23, 1999, vol. 3659, No. II, 1999, pp. 560–571.

Somenkov VA, et al., "Refraction Contrast in X–Ray Introscopy", Soviet Physics Technical Physics, US, American Institute of Physics, NY, vol. 36, No. 11, Nov. 1, 1991, pp. 1309–1311.

*Primary Examiner*—Craig E. Church
(74) *Attorney, Agent, or Firm*—Cantor Colburn LLP (57) ABSTRACT

A X-ray image forming method, comprising steps of: conducting a magnifying radiography by irradiating an object with divergent X-ray emitted from a X-ray tube; and forming a X-ray image by detecting X-ray passing through the object by a X-ray detector; wherein the magnifying radiography is conducted to satisfy the following formula: $9E \geq B$, where B is a width ($\mu$m) of a blurred portion of the X-ray image caused by penumbra and E is a width ($\mu$m) of an edge portion enhanced by X-ray refraction contrast.

21 Claims, 7 Drawing Sheets

X-RAY IMAGE RADIOGRAPHING METHOD AND X-RAY IMAGE RADIOGRAPHING APPARATUS

BACKGROUND OF THE INVENTION

The present invention relates to an X-ray image radiographing method and an X-ray image radiographing apparatus, and specifically to an X-ray image radiographing method and an X-ray image radiographing apparatus in which, when an X-ray tube to radiate the divergent X-ray is used and the magnifying radiography is conducted, the X-ray image having the excellent sharpness is obtained by the edge enhancement by the X-ray refraction contrast.

The X-ray image using an action in which the X-ray transmits the substance, is widely used for the medical image diagnosis and non-destructive inspection. This X-ray image is a shade and shadow image obtained from a fact that, when the X-ray transmits an object, an X-ray transmission amount is different depending on the value of the atomic weight of the substance constituting the object. That is, the two-dimensional distribution of the X-ray intensity which is radiated from the X-ray source and which transmits through the object, is detected by an X-ray image detector, and the X-ray image based on the X-ray absorption contrast of the object is formed.

Figure 1:
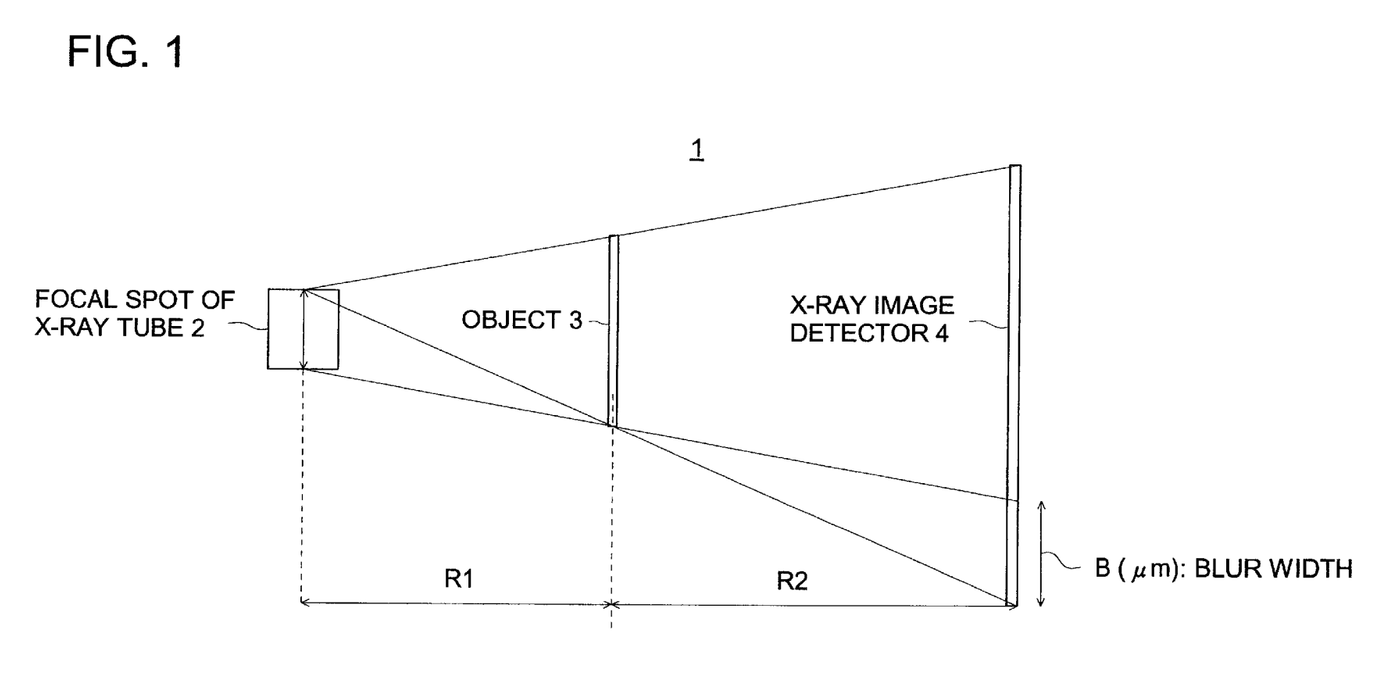
FIG. 1 is a view showing an X-ray image radiographing apparatus.

As an example of the X-ray tube which radiates the divergent X-ray used for the non-destructive inspection and in the general medical facility, there is a rotational anode X-ray tube, and in this X-ray tube, the X-ray generated when a thermoelectron collides with an anticathode spreads radially. By using this characteristic, by keeping the distance between the object and the X-ray image detector apart, the magnifying radiography of the X-ray image is conducted. At this time, because a size of focal spot of the X-ray is a finite value, it is well known that, in the magnifying radiography, as shown in FIG. 1, blurs called "penumbra" are generated.

When the X-ray source is a point light source, or when the X-ray source can be regarded as a point light source, that is, when the size of focal spot is 0, or almost 0, blurs are not generated in the X-ray image of such the magnifying radiography. On the one hand, when the sufficient X-ray intensity to transmit through the thick object such as a human body is tried to have, practically, a finite value of size of focal spot is necessary. Accordingly, in the Radiography, blurs due to this penumbra can not be avoided, and specifically, in the case of the magnifying radiography, the sharpness of the X-ray image is decreased.

Then, when the magnifying ratio of the magnifying radiography is increased, the width of the blur is further enlarged. For example, in the magnifying radiography such as the chest spot radiography, or the born portion accurate radiographing, when its magnifying ratio is increased, the sharpness of the image is deteriorated, therefore, radiographing becomes rather difficult, and the effect of the magnifying radiography is decreased to half.

On the one hand, the present inventors find that, when the object is radiographed, the edge enhancement phenomenon by the refraction contrast of the X-ray is generated at a portion having the refractive index of the object.

SUMMARY OF THE INVENTION

The present invention is attained in view of the foregoing problems, and its object is to provide an X-ray image radiographing method by which, when the magnifying radiography is conducted by using an X-ray tube which radiates divergent X-ray, by optimizing the relationship between the blur due to the penumbra and the edge enhancement, the magnifying radiographic image having the excellent sharpness can be obtained, and a radiographing apparatus using the method.

In order to solve the above problems and to attain the object, the present invention is structured as follows.

(1) An X-ray image radiographing method in which an X-ray tube to radiate a divergent X-ray is used, and the X-ray radiated from the X-ray tube is made to transmit the object and the magnifying radiography is conducted, and when the width of the blur due to the penumbra of the X-ray image obtained by the magnifying radiography is B ($\mu$m), and the width of the edge enhancement by the X-ray refraction contrast is E ($\mu$m), 9 E$\geq$B.

(2) The radiographing method according to (1), wherein the magnifying ratio of the magnifying radiography is 1.1–10 times.

(3) The radiographing method according to (1) or (2), wherein the size of focal spot of the X-ray tube is 0.03 mm–0.3 mm.

(4) The radiographing method according to any one of (1) to (3), wherein the X-ray tube voltage of the X-ray tube is 50 kVp–150 kVp.

(5) The radiographing method according to any one of (1) to (4), wherein the X-ray tube is a Coolidge X-ray tube.

(6) The radiographing method according to any one of (1) to (5), wherein the X-ray tube is a tungsten rotational anode X-ray tube.

(7) The radiographing method according to any one of (1) to (6), wherein a screen film system whose average gradient G is 1.5–4.0 is used, and the edge enhancement width E is not smaller than 9 $\mu$m.

(8) The radiographing method according to any one of (1) to (7), wherein a digital X-ray image detector whose pixel size is 1 $\mu$m–200 $\mu$m, is used, and the edge enhancement width E is not smaller than 0.1 $\mu$m.

(9) The radiographing method according to any one of (1) to (8), wherein the object is a human body or a medical sample taken out from the human body.

(10) An X-ray image radiographing apparatus, which having: the X-ray tube to radiate the divergent X-ray; an object position setting tool to set a position of the object to the X-ray tube; and the X-ray image detector to detect the X-ray image transmitted through the object, wherein, when the blur width due to the penumbra of the X-ray image is B ($\mu$m), and the edge enhancement width due to the X-ray refraction contrast is E ($\mu$m), and when the X-ray radiated from the X-ray tube is made to transmit the object and the magnifying radiography is conducted, the object position setting tool and the X-ray image detector can be arranged so that 9 E$\geq$B.

(11) The X-ray image radiographing apparatus according to (10), wherein the object position setting tool can be provided so that the distance between the X-ray tube and the object is apart not smaller than 0.5 m, and the distance from the object to the X-ray image detector can be apart not smaller than 1 m.

(12) The X-ray image radiographing apparatus according to (11), wherein the apparatus has a rail or a support provided with the information of the distance with the focus of the X-ray tube as the start point, and a holder for the X-ray image detector to hold the X-ray image detector, and wherein the object position setting tool and the holder for the X-ray image detector are provided on the rail or the support so that these can be moved and can temporarily be fixed.

(13) The X-ray image radiographing apparatus according to any one of (10)–(12), wherein the apparatus has the X-ray tube in which the tube voltage of 50 kVp–150 kVp can be set, and the object position setting tool is located at a position apart from the X-ray tube by not smaller than 0.5 m, and the X-ray image detector is located at a position apart from the object position setting tool by not smaller than 1 m.

(14) The X-ray image radiographing apparatus according to (10) to (13), wherein the magnifying ratio of the magnifying radiography is 1.1–10 times.

(15) The X-ray image radiographing apparatus according to any one of (10) to (14), wherein the size of focal spot of the X-ray tube is 0.03 mm–0.3 mm.

(16) The X-ray image radiographing apparatus according to any one of (10) to (15), wherein the X-ray tube is a Coolidge X-ray tube.

(17) The X-ray image radiographing apparatus according to any one of (10) to (16), wherein the X-ray tube is a tungsten rotational anode X-ray tube.

(18) The X-ray image radiographing apparatus according to any one of (10) to (17), wherein a screen film system whose average gradient G is 1.5–4.0 is used as the X-ray image detector, and the edge enhancement width E is not smaller than 9 $\mu$m.

(19) The X-ray image radiographing apparatus according to any one of (10) to (18), wherein the digital X-ray image detector whose pixel size is 1 $\mu$m–200 $\mu$m is used as the X-ray smaller than 0.1 $\mu$m.

DETAILED DESCRIPTION OF THE PREFERRED EMBODIMENT

In the present invention, in the X-ray image radiographing apparatus 1 shown in FIG. 1, the X-ray radiated from the Coolidge X-ray tube which is an example of an X-ray tube 2 radiating the divergent X-ray, is made to transmit an object 3, and the X-ray image is obtained by an X-ray image detector 4, and the magnifying radiography is conducted. Because the X-ray is an electromagnetic wave, the nature of the wave, that is, in the same manner as in the visible rays, when the X-ray transmits the material having the different refractive index, that is, the object 3, the X-ray has the nature that the refraction occurs on the interface. Incidentally, the magnifying radiography is a radiographing in which the image enlarged more than the object 3 is obtained on the X-ray image detector 4. The magnifying ratio in this case, means the enlargement to the length, and for example, in the system as shown in FIG. 1, the magnifying ratio (magnification) is defined as $(1+R_2/R_1)$.

Figure 2:
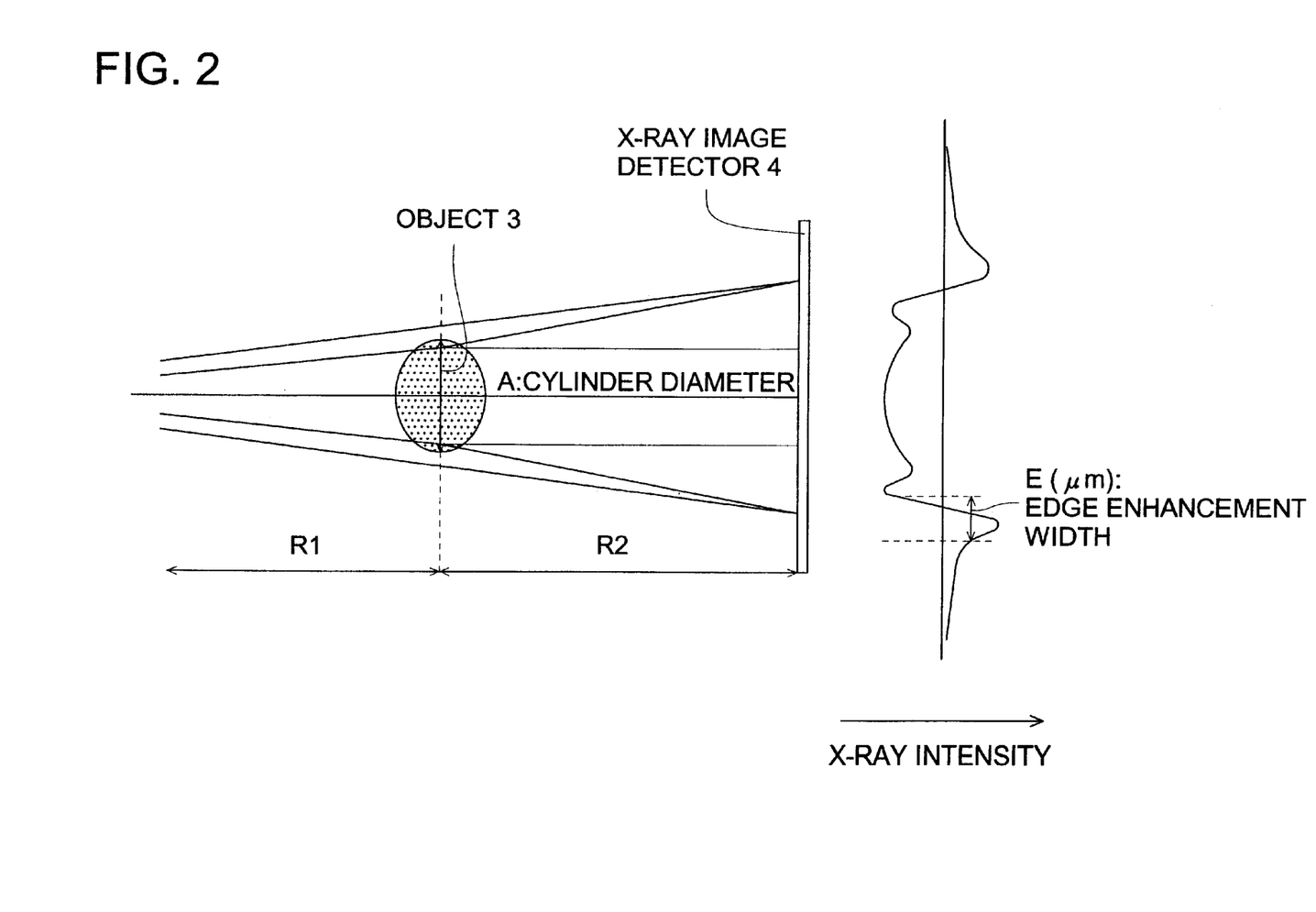
FIG. 2 is a view showing the edge enhancement of the X-ray image radiographing.

As typically shown in FIG. 2, in the X-ray transmission image on the X-ray image detector 4 of the interface portion having the different refractive index, a portion in which the X-ray intensity is decreased by the refraction of the X-ray, and a portion in which the X-ray intensity is increased when the refracted X-ray is overlapped with the X-ray straightly advanced in the space, are generated. That is, in the negative image obtained here, being bounded by the interface having the different refractive index, the density of a portion in which the X-ray intensity is decreased, is decreased to minimum, and a portion in which the X-ray intensity is increased, becomes blackish further, and as the result, so-called edge enhanced image is obtained This is a phenomenon called the X-ray refraction contrast. Because the wavelength of the X-ray is very short, and its refractive index is small, in the conventional X-ray image radiographing which is generally conducted, the X-ray refraction contrast is so weak that it is passed unmarked. That is, in the conventional X-ray image, the X-ray refraction contrast is not fully utilized, and for the X-ray image, only the absorption contrast by the absorption difference of the X-ray is applied.

In the present invention, this X-ray refraction contrast is used for a means for solving the problems. That is, even when the blur of the image due to the penumbra is generated in the magnifying radiography, by making the edge enhancement described above generate simultaneously, this blur is eliminated, and thereby, the enlarged radiographing image having the excellent sharpness is obtained. Further, specifically, in the present invention, the problems are solved by the following method.

That is, in the case where the magnifying radiography is conducted by using the X-ray tube 2 radiating the divergent X-ray, which is, for example, a Coolidge X-ray tube, when the blur width due to the penumbra is B ($\mu$m), and the edge enhancement width by the X-ray refraction contrast enhancement is E ($\mu$m), $$9E \geq B \qquad \text{(Equation 1)}$$

Incidentally, it is preferable that the magnifying ratio of the magnifying radiography herein is 1.1–10 times. It is preferable that the size of focal spot of the X-ray tube 2 used herein is 10 $\mu$m–1000 $\mu$m. Further, it is preferable that the X-ray tube voltage of the X-ray tube 2 is 50 kVp–150 kVp. It is preferable that the X-ray tube 2 includes tungsten in the anticathode.

Herein, the X-ray focus means a window viewed from the object direction, from which the X-ray generated when the electron beams collide with, for example, the rotational anode of the X-ray tube 2 is taken out. The size of the window is called the size of focal spot, and when the focus is the square, its one side length, and when the focus is the rectangle other than the square, its short side length, and when the focus is the circle, its diameter is the size of focal spot, and it can be measured as regulated in JISZ4704. Further, even in the case where the shape of the focus is the other one, as regulated in JISZ4704, it can be measured by using a pin hole camera or a test chart.

Figure 3:
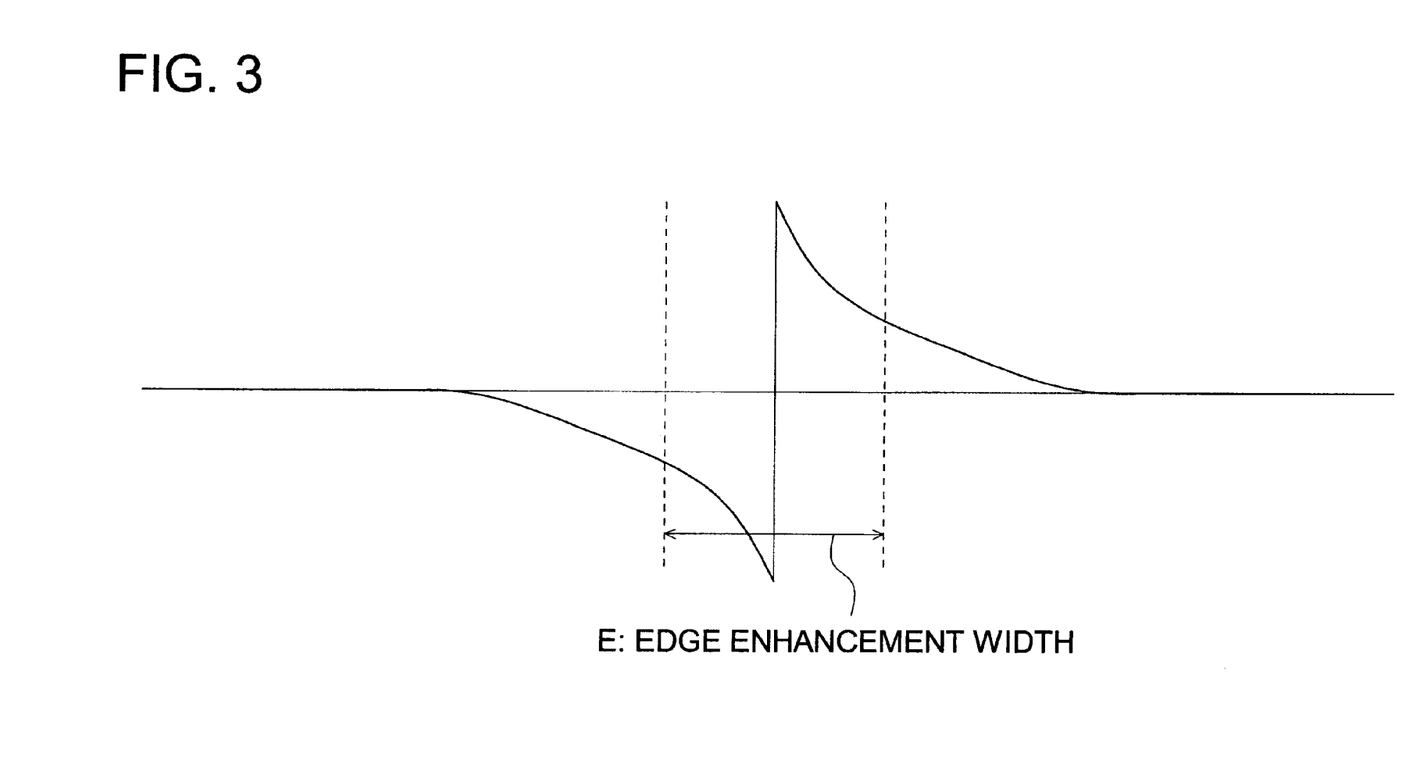
FIG. 3 is a view showing an intensity distribution of an edge portion.

It is preferable that, for the X-ray image detector 4 for forming the image, the screen film system whose average gradient G is 1.5–4.0 is used. In this case, it is preferable that the edge enhancement width E is, as shown in FIG. 3, not smaller than 9 $\mu$m. When it is. in this range, the accuracy of the diagnosis by the human visual sensation can be increased.

Further, when the digital X-ray image detector is used as the X-ray image detector 4, it is preferable that the image size is not smaller than 1 μm and not more than 200 μm, and it is preferable that the edge enhancement width E at this time is not smaller than 0.1 μm. When it is in this range, the accuracy of the diagnosis can be increased.

In the present. invention, it is specifically preferable that the object 3 is the human body or the inspection sample picked from the human body. The detail will be further described below.

Initially, as the X-ray source used in the present invention, the X-ray tube which radially radiates the X-ray, is used. In the X-ray tube radially radiating the X-ray, the magnifying ratio of the X-ray image can be arbitrarily set by adjusting the distance between the object and the X-ray image detector. The X-ray source used in the present invention is a Coolidge X-ray tube in which specifically, the X-ray is obtained when the thermal electrons collide with the anticathode, and in order to obtain specifically strong X-ray, the X-ray tube with the rotational anode is preferable. Then, the self-bias X-ray tube or plasma X-ray tube can be used.

The blur width B (μm) due to the penumbra is, as shown in FIG. 1, uniquely decided geometric optically, when the X-ray tube size of focal spot is D (μm), the distance from the X-ray focus to the object 3 is R1 (m), and the distance from the object 3 to the X-ray image detector 4 is R2 (m). That is, it can be calculated by the following equation, $$B = D \times (R2/R1) \quad \text{(Equation 2)}.$$

The edge enhancement width E (μm) of the interface due to the X-ray refraction contrast is, as shown in FIG. 2, a half value width of the X-ray intensity lowering maximum value and the X-ray intensity increasing maximum value, and as this value, the value obtained by the following equation can be used.

$$E = 39 \times R2(1 + 0.045/R1) \times \lambda^2 \times \sqrt{A} \quad \text{(Equation 3)}$$

In this case, R1 is the distance (m) from the X-ray source to the object 3, R2 is the distance (m) from the object 3 to the X-ray image detector 4, λ is the wavelength (A) of the maximum value of the X-ray intensity, and A is a diameter (mm) of the circle of the cross section when the object 3 material body is regarded as a column. This experimental equation is obtained as follows.

Initially, the intensity distribution as the reference is obtained as a model by the light beam tracking under the following conditions.

Model: plastic fiber with the 1 mm diameter,

The difference of the refractive index to the air: $3 \times 10^{-6}$, (a value to the 1.5 Å of the Cu characteristic X-ray of the plastic), The arrangement: R1: infinity, R2=0.25.

The intensity distribution of the obtained edge portion is shown in FIG. 3. In contrast to this, it is found that the X-ray refraction contrast width (edge enhancement width) E is proportional to each of R2, refractive index difference and the square root of the diameter of the material body, and further, the increasing amount of the edge enhancement width E, when R1 is definite, is proportional to 1/R1.

Herein, the refractive index difference is proportional to the second power of the wavelength (λ) in the X-ray area. Accordingly, the equation of $E = a \times R2 \times (1 + b/R1) \times \lambda^2 \times \sqrt{A}$ can be described. Where, a and b are constants. Next, from the practical point of view, from the edge enhancement width E in the intensity distribution obtained by the computer simulation, a=39, and b=0.045, are obtained, and finally, (Equation 3) is obtained.

Further, as a value of the edge enhancement width E, the values obtained from the following equation can also be used.

$$E = 2.7 \times (1 + R2/R1)^{1/3} \times (\lambda^2 \times R2 \times \sqrt{A})^{2/3} \quad \text{(Equation 4)}$$

In this case, R1 is the distance (m) from the X-ray source to the object 3, R2 is the distance (m) from the object 3 to the X-ray image detector 4, λ is the wavelength (A) of the maximum value of the X-ray intensity, and A is the diameter (mm) of the circle of the cross section when the material body of the object 3 is regarded as a column.

More generally, the edge enhancement width of the interface by the X-ray phase contrast is, as shown in FIG. 2, the half value width of the X-ray intensity lowering maximum value and the X-ray intensity increasing maximum value, and this value can be obtained, in the case of the column-like material body placed in the air, by the theoretical equation $E = 2.3 \times (1 + R2/R1)^{1/3} \times (R2 \times \delta \times \sqrt{A})^{2/3}$.

In this case, δ is the difference of the refractive index (δ>0) between the material body and the air, This theoretical equation is obtained from that, when the wave front shape after the transmission through the material body is W, the intensity distribution caused by the X-ray refracted by the material body is expressed by using the two times differential W" of W, as $i = (1 + R2/R1)/(1 - R2 \times W")$.

δ is expressed as the function of λ(A), and to the component of the human body, it can be expressed as the equation 3.

All of the above equations are obtained by considering the refraction effect of the X-ray.

Further, the value obtained by the (Equation 4) is nearer to the true edge enhancement width than the value obtained by the (Equation 3), and more preferable.

In Japanese Tokuhyohei No. 11-50262 or the science magazine "Nature, vol. 77, 2962 (1996)", the edge enhancement effect of the X-ray image due to the interference of the X-ray is discussed. In this discussion, initially, it is the presupposition that the X-ray to be used has the high lateral spatial coherence, and the edge enhancement effect is due to the interference of the X-ray, that is, due to the decrease and increase of the intensity of the X-ray by the first approximation of the Fresnel diffraction contrast. Accordingly, it is discussed that: in order to obtain the X-ray of the high spatial coherence, it is necessary that the distance from the object to the X-ray image detector is taken sufficiently long so that the size of focal spot of the X-ray is so small as possible and it can be regarded as a point light source, and because the contrast directly changes to the distance (R2) between the object and the X-ray image detector, it is necessary that the distance longer than an infinite value is taken for R2.

In the present invention, because the contrast enhancement phenomenon by the refraction of the X-ray is used, the high spatial coherence of the X-ray is not specifically necessary. Accordingly, for the size of focal spot, it is not always necessary that it is the point light source or it is so small as can be regarded as the point light source. Further, in the present invention, the distance (R1) from the X-ray source to the object, and the distance (R2) between the object and the X-ray image detector are determined from the magnifying ratio of the X-ray image or other factors. Further, R1 and R2 are determined by the (Equation 2) expressing the relationship between the edge width obtained from the (Equation 3) or (Equation 4) and the geometric-optically obtained blur width. As described above, the spatial coherence of the X-ray is not specifically necessary for the resolution of the problems of the present invention, and the high contrast can not be realized only by the distance (R2) between the object and the x-ray image detector. Accordingly, the effect obtained by the present invention is different from the technology disclosed in the above patent publication and the science magazine.

Further, in order to obtain the X-ray image with the excellent sharpness, a method by which the scattered X-rays are removed by separating the X-ray image detector apart from the object, is known as. a Groedel effect. Specifically, when the magnifying radiography is conducted, because its distance becomes large, the Groedel effect is used. On the one hand, because the X-ray refraction contrast according to the present invention does not specifically relate to this scattered X-rays, in the relational expressions during the introduction process of (Equation 3) and (Equation 4), factors relating to the X-ray scattering are not included. That is, the present invention is different from the conventionally known Groedel effect by which the scattered X-rays are removed and the sharpness of the X-ray image is increased.

However, also in the present invention, when the scattered X-rays become problem, for example, in the case where the X-ray grid to remove the scattered X-rays is not used, when the distance between the object and the X-ray image detector is set, it is of course that the influence of the scattered X-rays may also be considered.

From the (Equation 2), the smaller the size of focal spot of the X-ray tube is, the smaller the blur width is. In this case, the X-ray refraction contrast is more intensely observed. However, when the size of focal spot is small, because the X-ray intensity from the X-ray source is decreased, the object 3 and the X-ray image detector 4 have limitations. On the one hand, when the size of focal spot is increased, the X-ray intensity is increased, however, because the blur width B due to the penumbra is increased, it is difficult to obtain the X-ray refraction contrast effect. Accordingly, from such the balance, it is preferable that the size of focal spot is at least 0.03 mm–0.3 mm.

In the present invention, it is preferable that the distance R1 from the focus of the X-ray tube is not smaller than 0.15 m, and the distance R2 between the object 3 and the X-ray detector 4 is not smaller than 0.15 m. When R1 is not smaller than 0.15 m, the geometrical distortion is more decreased in the X-ray image. Further, when R2 is not smaller than 0.15 m, it is difficult that the scattered X-rays by the object are picked up, and the sharpness of the image by the scattered X-rays is more increased.

In the present invention, the X-ray which reaches the X-ray image detector 4, is decreased because the magnifying radiography is conducted. Accordingly, it is preferable that the X-ray grid for removing the scattered X-rays which accompanied by the loss of the X-ray, is not used. Further, when the object 3 is thick, it is preferable that both of R1 and R2 are not smaller than 0.5 m. Further, when it is used for the medical uses, from the view point of the X-ray exposure, it is desirable that the distance R1 from the X-ray source to the object is not smaller than 1 m, and the distance R1+R2 between the X-ray source and the X-ray image detector is not smaller than 1.5 m. When the dimensions of the X-ray image radiographing room or the X-ray intensity arriving at the X-ray image detector 4 are considered, it is preferable that R1+R2 is within the distance of 10 m, and further, it is more preferable that R1+R2 is within the distance of 5 m.

In the (Equation 3) and the (Equation 4), the diameter A of the detection material in the position of the object 3 is a value to be determined according to the purpose to desire to form the image by the radiographing. In the non-destructive inspection, it is necessary to search the cracking of about 0.1 mm width, or for the medical uses, it is desired to form the image of the tumor or the calcification shadow of the size of about 1 mm, for example, for the detection of initial lung cancer of the chest portion. Specifically, the magnifying radiography of the present invention is effective for the detection of the structure smaller than 10 mm.

As described above, the value A in the (Equation 3) and the (Equation 4), is a value to be determined according to the purpose of the radiographing, and in the present invention, it is considered that the A is not smaller than 0.1 mm and not larger than 10 mm, and further, not smaller than 1 mm and not larger than 2 mm.

Figure 4:
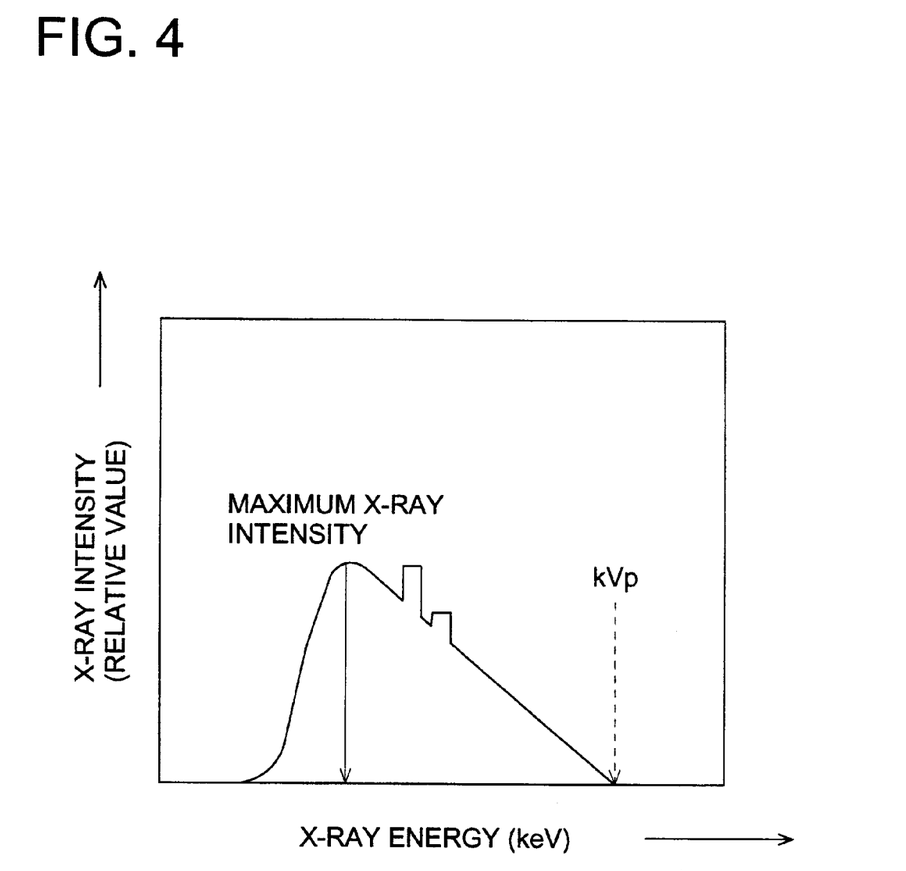
FIG. 4 is a view showing an index of the X-ray energy radiated from an X-ray tube.

As shown in (Equation 3) and (Equation 4), the edge enhancement width E depends on the wavelength of the used X-ray. The wavelength $\lambda$ (A) in (Equation 3) and (Equation 4) is the X-ray wavelength of the maximum value of the X-ray intensity of the continuous spectrum except the characteristic X-ray generated from the used X-ray tube. For example, in the Coolidge X-ray tube 2 having tungsten as the rotational anode, it is calculated as $\lambda$=0.4 angstrom (FIG. 4).

Depending on the tube voltage of the used X-ray tube, the quality of radiation of the X-ray, that is, the easiness of transmission to the object is different. Because higher the tube voltage is, the more the generated X-ray energy component is increased, the X-ray easily transmits the object, thereby, the X-ray image contrast due to the absorption is lowered. When the tube voltage is low, the X-ray hardly transmits the object. Accordingly, it is necessary that the tube voltage of the X-ray tube is set depending on the purpose of use. For the X-ray image diagnosis for the medical uses or the non-destructive inspection, the range of the X-ray tube voltage of 50 kVp–150 kVp is used.

An area of the (Equation 1) of the present invention is an area appropriate for these X-ray energy area. Herein, "kVp" expresses the X-ray component of the highest energy of the radiated X-ray, and generally, it is an index of the X-ray energy radiated from the X-ray tube, and is set as the X-ray tube voltage at the radiographing (FIG. 4).

Figure 5:
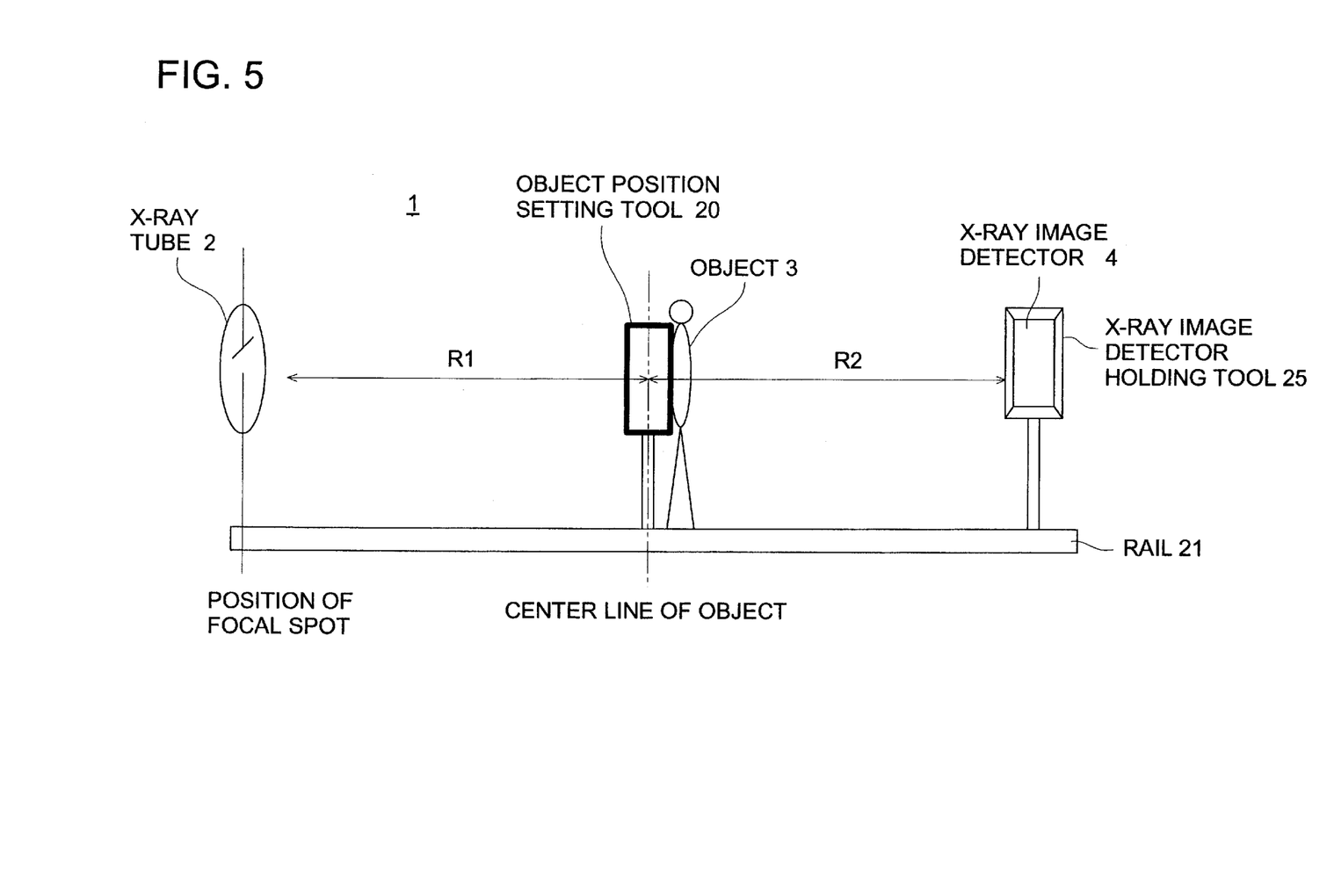
FIG. 5 is a view typically showing a horizontal type X-ray image radiographing apparatus.
Figure 6:
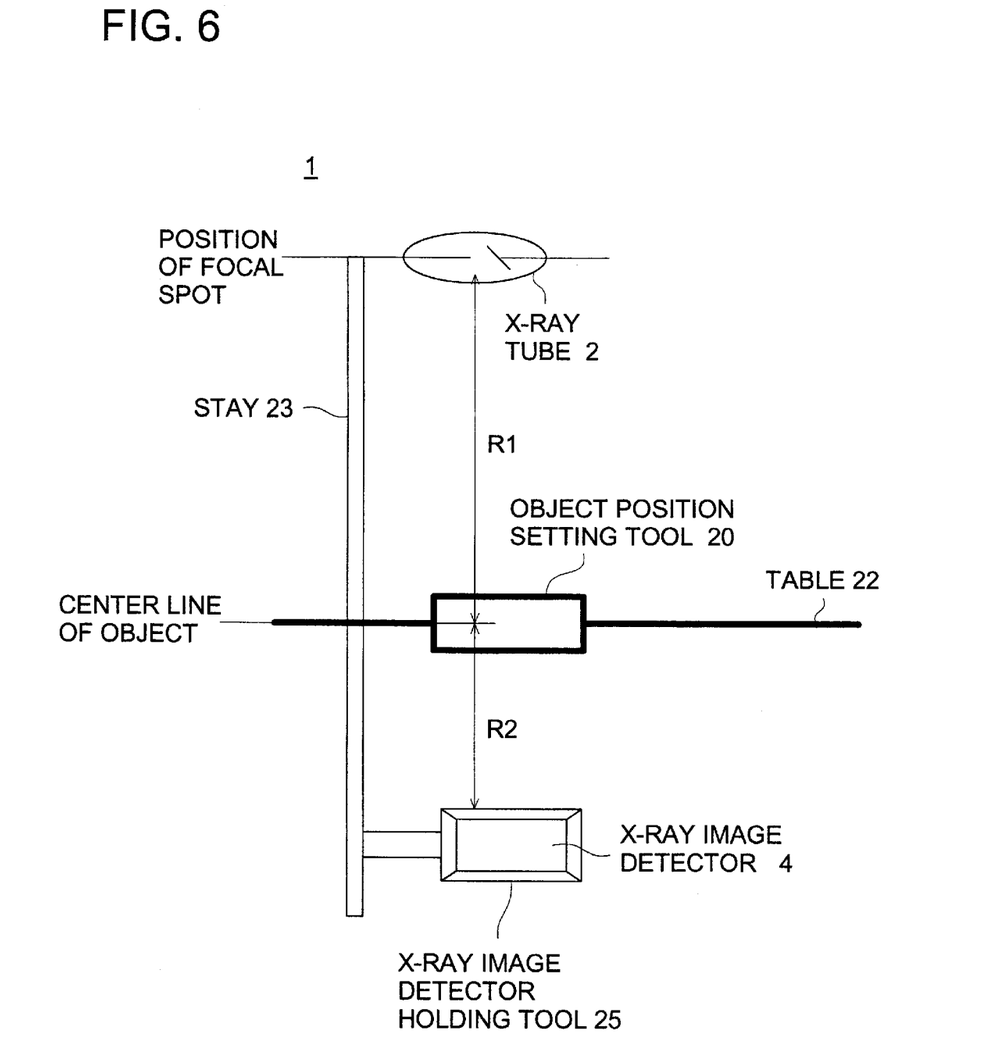
FIG. 6 is a view typically showing a vertical type X-ray image radiographing apparatus.

In FIG. 5 and FIG. 6, the horizontal type and the vertical type X-ray image radiographing apparatus in the present invention will be typically shown. When the magnifying radiography is conducted in the X-ray image radiographing apparatus 1, the blur due to the movement of the object 3 is also enlarged. Accordingly, in order to decrease such the blur as much as possible, an object position fixing tool 20 to fix the object 3 at the radiographing, is necessary. It is preferable for providing the mechanical strength that the object position fixing tool 20 has a frame made of metals or reinforced plastic resins, and in the inside of the frame through which the X-ray transmits, it is preferable that the plastic resin plate to transmits the X-ray as much as possible is adhered. It is preferable that the thickness of the plate is 0.05 mm–several mm. When a body or a portion of the body of a patient as the object 3 is closely fixed onto the object position fixing tool 20, the movement of the patient at the radiographing can be made to the minimum.

The distance R1 from the position of the focus of the X-ray tube 2 to the object position fixing tool 20, and the distance R2 from the object position fixing tool 20 to the X-ray image detector 4 can be arbitrarily set in the scope of the present invention. In order to conduct the setting correctly, it is preferable that the rail 21 on which the distance is stamped, having the distance information from the focus of the X-ray tube 2 as the start point, connecting the X-ray tube 2, object position fixing tool 20, to X-ray image detector 4, is provided. The X-ray image detector 4 and the x-ray image detector holding tool 25 are provided so that these can be moved on the rail 21 and can be temporarily fixed to it.

In FIG. 6, the X-ray tube 2 is provided above the object 3, however, in reverse to it, the X-ray tube 2 may be arranged below, and the X-ray image detector 4 may be arranged above. In this apparatus, it is preferable that a table 22 is provided so that the patient as the object 3 can be radiographed under the lying condition. Onto the table 22, the object position setting tool 20 is provided. Further, in the same manner as in FIG. 5, in order to correctly set the distance R1 from the X-ray tube 2 to the object 3 and the distance R2 from the object 3 to the X-ray image detector 4, it is preferable that the pole 23 with the distance stamp is provided. The X-ray image detector 4 and an X-ray image detector holding tool 25 are arranged so that these can be moved on the pole 23, and can be temporarily fixed to it.

Incidentally, as the object position setting tool 20, an example to hold the object is shown, however, even when the object is not held, it may be a tool by which the object position necessary for obtaining the X-ray image of the present invention is determined, or may be a member to indicate the object position.

Nowadays, various kinds of detectors are used as the X-ray image detector 4. For example, the photographic photosensitive material on which silver halide emulsion is coated, and the screen film system composed of the X-ray fluorescent intensifying screen can be used. As the photographic photosensitive material (film), the material in which the emulsion layer is coated on the one side or both sides of the support material, can be used. When the high resolving power is necessary, it is preferable that the single-coated film is used, and when the magnifying ratio is large, it is preferable that the high sensitivity double-coated coating film is used. For the fluorescent intensifying screen(screen) used together with the photographic photosensitive material, the screen in which blue is light emitted or green is light emitted by the X-ray irradiation, can be used. Specifically, the fluorescent screen consisting of gadolinium oxy-sulfide ($Gd_2O_2S$: Tb, hereinafter defined as GOS) fluorescent material activated by terbium having the good X-ray absorption factor, is preferable. It is preferable that the average gradient G of the screen film system to be used, is 1.5–4.0. Further, because the X-ray image contrast is increased by the edge enhancement effect, it is more preferable that the average gradient G of the screen film system is from 2 to 3.8, and further, the system whose latitude is wide in an area lower than "fog density+1", is preferable. Incidentally, the average gradient G means the inclination of the straight line connecting a point of the density of "fog density+0.25" with a point of the density of "fog density+2.0". The fog is the density obtained by developing a portion which is not exposed.

Incidentally, the characteristic curve applied herein, is used when the silver halide photographic photosensitive material is used, and for example, as described in "Revised the Basis of Photographic Engineering—silver halide photography edition—" (edited by The Society of Photographic Science and Technology of Japan, published by Corona co., 1998), it is the D–log E curve in which the blackening density(optical density)D of the photographic image obtained by the developing processing after the emulsion layer of silver halide is exposed, is plotted to common logarithm of the exposure amount E (=I×t, I is exposure illuminance, t is the exposure time).

As the primary factor influencing on the average gradient of the screen film system, two of the characteristic of the film and its developing processing are listed. In the case of the film, the average gradient is determined by the composition or particle size distribution of the silver halide particle constituting the emulsion layer, additive agent such as fog inhibitor, further an amount of silver halide particles in the emulsion layer. For the silver halide photographic photosensitive material used in the present invention, its outline is described in, for example, the above "Revised the Basis of Photographic Engineering—silver halide photography edition—" (edited by The Society of Photographic Science and Technology of Japan, published by Corona co., 1998). Further, for the developing processing, the average gradient can be increased by increasing the development processing temperature or extending its processing time, however, when the automatic development processing is conducted, principally, it is preferable that it is processed by the development processing condition specified by the film manufacturer.

Incidentally, it is necessary that the image resolving power of the screen film system is larger than the edge enhancement width E. Further, in the medical image in the screen film system, because generally the film image is directly observed by the naked eye, when the edge enhancement width is too narrow, the observation can not be conducted. Accordingly, as the result of the deep consideration, it is experimentally found that, when the screen film system is used as the X-ray image detector, the edge enhancement width E is preferably not smaller than 9 $\mu$m.

The digital X-ray image detector is a detector in which the X-ray image is obtained as a digital image signal, and for example, there are following detectors: the computed radiography (CR) using the imaging plate on which stimulable fluorescent material is coated; flat type X-ray image detector (FPD) in which the light generated when the X-ray irradiation is received by GOS or cesium iodide fluorescent material, is converted into the electric signal by using the photodiode and read by the TFT, or the electric charges generated when the X-ray irradiation is received by a-Se, is directly read by the TFT; or detector which reads the visible rays by the CCD or CMOS by converting the X-ray image obtained by the X-ray irradiation into the visible rays by the GOS fluorescent material.

In the photographic system using these digital X-ray image detectors, the two dimensional plane is divided and the X-ray image information is read. The length of a side of the quadrangle of the minimum area to be read, or the diameter of the circle is called the pixel size. For example, in the above CR, it corresponds to a pitch when the stimulative light emission is read, or in the minimum reading diameter of the CCD or CMOS, or FPD, it corresponds to a reading diameter of the silicon photo diode, or the minimum pixel size to collect the generated electric charge in the X-ray conductive layer.

Figure 7:
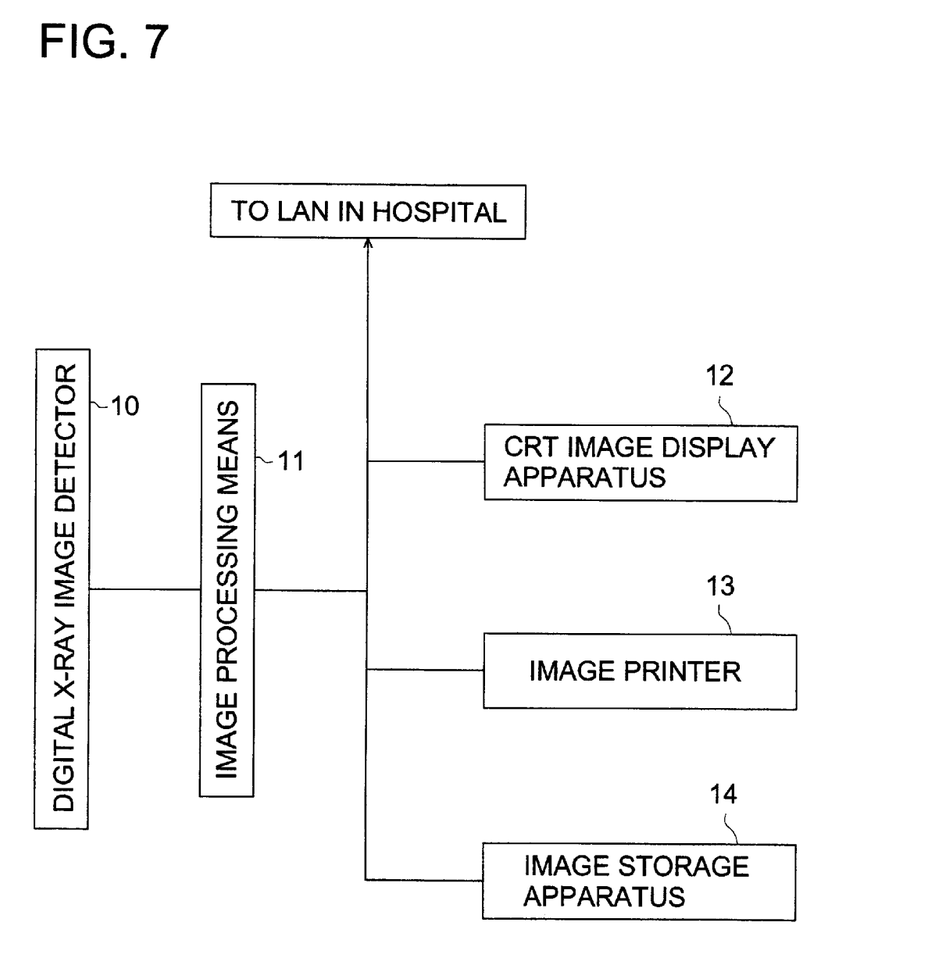
FIG. 7 is a view showing an output system of the X-ray image using a digital X-ray image detector.

Further, as shown in FIG. 7, when the digital X-ray image detector 10 is used, the image processing is conducted by the image processing means 11, and by this image processing, the enlargement, reduction, or adjustment of the image contrast can be easily conducted, and the image is outputted to the CRT image display apparatus 12, or image printer 13, and for example, sent to LAN in the hospital. As described above, when the digital X-ray image detector 10 is used, after the magnifying radiography of the present invention, the image can be displayed by reducing it to the practical image size. Further, the image can be enlarged more than the magnifying ratio at the time of radiographing. When the enlargement more than the magnifying ratio at the time of the radiographing, is considered, it is preferable that, in the digital X-ray image detector 10, the edge enhancement width E to be read is not smaller than 0.1 $\mu$m. Herein, in the digital X-ray image detector 4, the reading minimum image size is determined according to the purpose of use or the ability of the system.

In the present invention, when the stimulable fluorescent material is used for the X-ray image detection, generally, the reading of the image signal is conducted by the laser exposure scanning. Ordinarily, the minimum pixel size is equal to the reading laser spot diameter. For this diameter, it is preferable that it is not smaller than 1 μm, however, in order to increase the reading speed, it is more preferable that the diameter is not smaller than 20 μm. Further, in order to increase the sharpness of the reading image itself, it is preferable that the diameter is not more than 200 μm. Further, this is the same for the other digital X-ray image detectors described in the present invention.

As the X-ray tube, it is preferable that tungsten is included in the anticathode as the anode, which is widely used presently in the medical job-site. It is because, for obtaining the X-ray image of the non-destructive inspection or human body, the most preferable X-ray energy range can be obtained. When the small animals such as fish which has better X-ray permeability is the object, the X-ray source, for example, whose anode is copper is used.

In the present invention, there is a possibility that it can contribute to, for example, the detection of the initial lung cancer smaller than 5 mm of the chest portion. It is because, when magnifying radiography of 8 times is conducted, the structure whose dimension is 2 mm, is pictured by being enlarged to 16 mm. Conventionally, when such large magnifying radiography is conducted, the decipherment is difficult on the contrary due to the blur by the penumbra, however, in the present-invention, the fine structure can be sharply pictured, thereby, the decipherment becomes easy.

Further, for early detection of the metabolic and rheumatic sickness, the magnifying radiography of the peripheral bone of the finger is conducted. In this case, in order to attach great importance to the sharpness, a method in which the non-screen radiographing in which the X-ray fluorescent intensifying screen (screen) is not used, is conducted, and enlargement print is conducted, is known. When the non-screen radiographing is conducted, it is a problem that the X-ray exposure amount is large.

In the present invention, the magnifying radiography whose dose is lower than in the non-screen radiographing, and which has good sharpness, can be realized. In today's medical job-site, the X-ray of 50 kVp–150 kVp of the tungsten X-ray tube is widely used. Then, when the screen film system is applied on the X-ray image detector, it can be easily introduced into the medical job-site. Accordingly, the present invention is specifically effective for the application to the medical field.

EXAMPLE 1

As the X-ray source, the X-ray tube L662202 made by Hamamatsu Photonics co., in which the size of focal spot is 40 μm, and the anti-cathode is the tungsten anode, and the X-ray tube DRA-3535HD made by Toshiba Electric co., in which the anticathode is the tungsten anode, and the size of focal spot is 300 μm, are used, and the chest portion phantom image made by Kyoto kagaku co., is radiographed. The X-ray tube voltage in this case is 120 kVp for the both. The arrangement of the equipment of the X-ray image photographic apparatus is as shown in FIG. 5. The frame of the object position setting tool is 2 cm width vinyl-chloride, and about 0.2 mm thick transparent polyester film is adhered in the frame. The chest portion phantom is closely attached to the object position setting tool, and radiographed.

As the X-ray image detector, the screen film system is used. As the film, the medical use roentgen film SRIC made by Konica Corporation, in which iodide silver bromide emulsion is coated on the one side of the film support material, and the medical use roentgen film SRG made by Konica Corporation, in which iodide silver bromide emulsion is coated on the two-sides of the film support material, are used. As the fluorescent intensifying screen, SRO125 back use intensifying screen made by Konica Corporation, is used in combination with SRIC.

Further, as the double coated film SRG, the intensifying screen SRO250 or SRO1000, made by Konica Corporation, is used. The combination of SRO125 with SRIC has the lowest sensitivity, but, is a system having the highest resolving power. The sensitivity of the fluorescent intensifying screen combined with SRG is higher as Arabic numerals are increased, and on one hand, its resolving power is lowered. Incidentally, the average gradient G of SRIC is 2.6, and the average gradient G of SRG is 2.45.

The film development processing after the X-ray image radiographing, is conducted by the SRX502 automatic processor, made by Konica corporation, at 35° C. for 90 sec. After the development processing, the film is placed on the viewing box (light box) of about 9000 lux luminosity, and observed by the naked eye, and judged whether the edge enhancement is noticed.

That is, it is judged whether the black frames are pictured around an image of the cylindrical suspected blood vessels positioned almost in parallel to the film surface of the chest portion lung area. The diameter of the suspected blood vessels is used for the value of A in the equation 3. The rank of the judgement is a value estimated as follows: when it is visible very well, 5; when visible well, 4; when noticeable, 3; when it is visible, but, very weakly, 2; and when invisible, 1. The result is shown in Table 1. Incidentally, as E, the value obtained by using the (Equation 4) is shown.

TABLE 1

| No. | Intensifying screen/Film | R1 (m) | R2 (m) | Magnifying ratio | Focus size (μm) | B (μm) | Blood vessel dia. (mm) | E (μm) | 9 E (μm) | Judgement | mAs value |
|---|---|---|---|---|---|---|---|---|---|---|---|
| 1 | SRO250/SRG | 0.5 | 3.5 | 8 | 40 | 280 | 2 | 46 | 416 | 5 | 7.2 |
| 2 | SRO1000/SRG | 0.5 | 3.5 | 8 | 40 | 280 | 2 | 46 | 416 | 4 | 1.8 |
| 3 | SRO250/SRG | 1 | 1 | 2 | 40 | 40 | 1.5 | 11 | 103 | 4 | 1.8 |
| 4 | SRO125/SRIC | 0.5 | 0.5 | 2 | 40 | 40 | 1.5 | 7 | 65 | 3 | 1.8 |
| 5 | SRO250/SRG | 2 | 2 | 2 | 300 | 300 | 8 | 32 | 286 | 2 | 7.2 |
| 6 | SRO250/SRG | 1 | 1 | 2 | 300 | 300 | 1.5 | 11 | 103 | 1 | 1.8 |

Incidentally, the diameter of the blood vessels is measured by the radiographing when the magnifying radiography is not conducted. Because the sample No. 6 does not satisfy $9E \geq B$, the judgement result is 1, which is the lowest value.

Further, in the sample No. 5, the value E obtained by the (Equation 4) is as shown in the Table 1, however, the value E obtained by the (Equation 3) is 36 and 9E is 324, and satisfies 9E≧B.

EXAMPLE 2

In the same manner as in Example 1, the radiographing is conducted on the chest portion phantom X-ray image. The image signal is read by using the stimulable fluorescent material made by Konica corporation, at the laser spot size of 87 μm, and printed on the single coated film 67LP, made by Konica corporation, by the laser imager Li-7 made by Konica corporation, and development processed by the automatic processor SRX502. When the photographic condition is: R1=R2=2 m, the magnifying ratio is 2 times, size of focal spot is 40 μm, the blur width B=40 μm, and A of the (Equation 4) is the blood vessel diameter 1 mm, then, the edge enhancement width E=16 μm, 9E=144 μm, and 9E≧B, and E is larger than 0.1 μm.

The image obtained after radiographing, is enlarged to 3 times, and reduced to the original size, and then, the image is printed. In both prints, the periphery of the suspected blood vessel of 1 mm diameter, which is positioned laterally, is framed blackish, and the edge enhancement is noticed, and the judgement is 5 in the three-time enlarged image, and 4 in the original size display. Incidentally, the X-ray intensity is 7.8 mAs.

EXAMPLE 3

The radiographing of the cranium bone X-ray image is conducted by using the phantom of the head portion made by Kyoto Kagaku co. In this case, the setting tube voltage of the X-ray tube is 70 kVp. As the intensifying screen, SRO250 is used, and as the film, SRG is used. When the magnifying ratio at R1=R2=2 m is 2 times, size of focal spot is 40 μm, and the blur width B=40 μm, and the object width of A in the equation 3 is 1 mm, then, the edge enhancement width E=16 μm and 9E=144 μm, and 9E≧B. Further, it satisfies E≧9 μm. After the development processing in the same manner as in Example 1, when the image is observed by the naked eye on the viewing box, the border line which is framed blackish is observed clearly on the border portion of the bone portion. The estimation is 4. The X-ray intensity in this case is 36 mAs.

EXAMPLE 4

The radiographing of the finger bone X-ray image is conducted by using the phantom of the hand portion made by Kyoto Kagaku co. The arrangement of the equipment of the X-ray image radiographing apparatus is as shown in FIG. 6. A hole is made through a portion of the table, and about 0.5 mm thick transparent polyester plate is spread on the window, and the hand phantom is placed on it and radiographing is conducted.

In this case, the setting tube voltage of the X-ray tube is 50 kVp. As the intensifying screen, M100 made by Konica corporation is used, and as the film, single coated film CMH made by Konica corporation is used. The average gradient of this system is 3.2. After the-development processing in the same manner as in Example 1, when 1 mm wide (the value of A in the equation 4) bone is observed by the naked eye on the viewing box, and the result of the estimation is shown in Table 2.

TABLE 2

| No. | R1 (m) | R2 (m) | Magnifying ratio | B (μm) | Bone (mm) | E (μm) | 9E (μm) | Judgement | mAs value |
|---|---|---|---|---|---|---|---|---|---|
| 7 | 0.25 | 0.25 | 2 | 40 | 1 | 4 | 36 | 1 | 1.2 |
| 8 | 0.5 | 0.5 | 2 | 40 | 1 | 6 | 57 | 2 | 6 |
| 9 | 1 | 1 | 2 | 40 | 1 | 10 | 90 | 3 | 24 |
| 10 | 2 | 2 | 2 | 40 | 1 | 16 | 143 | 4 | 108 |

Nos. 9 and 10 are the judgment of "recognizable" (3), and "visible well" (4).

No. 7 does not satisfy 9E≧B, and the judgment is "invisible" (1), and No. 8 satisfies 9E≧B, but, does not satisfy E≧9 μm, and the judgment is "extremely weak" (2).

As described above, in the X-ray image radiographing method and the X-ray image radiographing apparatus of the present invention, when the magnifying radiography is conducted by using the X-ray tube radiating the divergent X-ray, by optimizing the relationship between the blur due to the penumbra and the edge enhancement, the magnifying radiography image having the excellent sharpness can be obtained.

What is claimed is:

1. A X-ray image forming method, comprising steps of:
    conducting a magnifying radiography by irradiating an object with divergent X-ray emitted from a X-ray tube; and
    forming a X-ray image by detecting X-ray passing through the object by a X-ray detector;
    wherein the magnifying radiography is conducted to satisfy the following formula:

$$9E \geq B$$

where B is a width (μm) of a blurred portion of the X-ray image caused by penumbra and E is a width (μm) of an edge portion enhanced by X-ray refraction contrast.

2. The X-ray image forming method of claim 1, wherein B is the width of the blurred portion of the X-ray image caused by penumbra on the X-ray image formed by the X-ray detector, and E is the width of the edge portion enhanced on the X-ray image formed by the X-ray detector.

3. The X-ray image forming method of claim 1, wherein a magnifying ratio of the magnifying radiography is 1.1 to 10.

4. The X-ray image forming method of claim 1, wherein a size of a focal spot of the X-ray tube is 0.03 mm to 0.3 mm.

5. The X-ray image forming method of claim 1, wherein a X-ray tube voltage of the X-ray tube is 50 kVp to 150 kVp.

6. The X-ray image forming method of claim 1, wherein the X-ray tube is a Coolidge X-ray tube.

7. The X-ray image forming method of claim 1, wherein the X-ray tube is a tungsten rotational anode X-ray tube.

8. The X-ray image forming method of claim 1, wherein a screen film system having an average gradation G of 1.5 to 4.0 is used as the X-ray detector and the width E of the enhanced edge portion is not smaller than 9 μm.

9. The X-ray image forming method of claim 1, wherein a digital X-ray image detector having a pixel size of 1 μm to 200 μm is used as the X-ray detector and the width E of the enhanced edge portion is not smaller than 0.1 μm.

10. The X-ray image forming method of claim 1, wherein the object is a human body or a medical sample taken out from a human body.

11. A X-ray image forming system, comprising:

a X-ray tube to emit divergent X-ray;

a setting device to set a position of an object in relation to the X-ray tube;

a detector to detect an X-ray image passing through the object;

the setting device and the detector arranged such that when a magnifying radiography is conducted by irradiating the object with the divergent X-ray emitted from the X-ray tube and by detecting X-ray passing the object, the following formula is satisfied:

$$9E \geq B$$

where B is a width ($\mu$m) of a blurred portion of the X-ray image caused by penumbra and E is a width ($\mu$m) of an edge portion enhanced by X-ray refraction contrast.

12. The X-ray image forming system of claim 11, wherein the setting device and the detector are arranged such that a distance between the X-ray tube and the object can be made longer than 0.5 m and a distance between the object and the detector can be made longer than 1 m.

13. The X-ray image forming system of claim 11, further comprising:

a support being one of a rail and a stay and provided with information regarding a distance from a focal spot of the X-ray tube; and a holder to hold the detector;

wherein the setting device and the holder are shiftable respectively along the support and are adapted to be fixed temporally on the support.

14. The X-ray image forming system of claim 11, wherein the X-ray tube can be set with a X-ray tube voltage of 50 kVp to 150 kVp, the setting device is located at a position distant 0.5 m or more from the X-ray tube, and the detector is located at a position distant 1 m or more from the setting device.

15. The X-ray image forming system of claim 11, wherein a magnifying ratio of the magnifying radiography is 1.1 to 10.

16. The X-ray image forming system of claim 11, wherein a size of a focal spot of the X-ray tube is 0.03 mm to 0.3 mm.

17. The X-ray image forming system of claim 11, wherein the X-ray tube is a Coolidge X-ray tube.

18. The X-ray image forming system of claim 11, wherein the X-ray tube is a tungsten rotational anode X-ray tube.

19. The X-ray image forming system of claim 11, wherein a screen film system having an average gradation G of 1.5 to 4.0 is used and the width E of the enhanced edge portion is not smaller than 9 $\mu$m.

20. The X-ray image forming system of claim 11, wherein the detector is a digital X-ray image detector having a pixel size of 1 $\mu$m to 200 $\mu$m and the width E of the enhanced edge portion is not smaller than 0.1 $\mu$m.

21. A X-ray image forming system, comprising:

a X-ray tube to emit divergent X-ray;

a first setting-device to set a portion of an object in relation to the X-ray tube;

a second setting device to set a detector for detecting an X-ray image passing through. the object, the first setting section and the second setting section arranged such that when a magnifying radiography is conducted by irradiating the object with the divergent X-ray emitted from the X-ray tube and by detecting X-ray passing the object, the following formula is satisfied:

$$9E \geq B$$

where B is a width ($\mu$m) of a blurred portion of the X-ray image caused by penumbra and E is a width ($\mu$m) of an edge portion enhanced by X-ray refraction contrast.

* * * * *

UNITED STATES PATENT AND TRADEMARK OFFICE
CERTIFICATE OF CORRECTION

PATENT NO. : 6,404,848 B1
APPLICATION NO. : 09/667009
DATED : June 11, 2002
INVENTOR(S) : Ishisaka et al.

It is certified that error appears in the above-identified patent and that said Letters Patent is hereby corrected as shown below:

Title Page (57) Abstract:
Line 3, after "from" delete "a" and insert therefor -- an --
Line 4, after "ing" delete "a" and insert therefor -- an --
Line 5, after "by" delete "a" and insert therefor -- an --
Column 1:
Line 44, after "tried" delete "to have"
Column 2:
Line 41, after "which" delete "hav-" and insert therefor -- has:--
Line 42, before "the" (first occurrence) delete "ing:"
Column 3:
Line 29, after "X-ray" insert therefor -- image detector, and the edge enhancement width E is not --
Column 4:
Line 13, after "obtained" insert therefor -- . --
Column 5:
Line 63, after "be" delete "described. Where," and insert therefor -- described, where --
Column 7:
Line 8, after "as" delete -- . --
Line 20, after "become" insert therefor -- a --
Line 35, after "such" delete "the" and insert therefor -- a --
Column 8:
Line 22, after, "Because" insert therefor -- the --
Line 32, after "for" delete "these" and insert therefor -- this --
Line 42, after "decrease" delete "such"
Line 49, after "to" delete "transmits" and insert therefor -- transmit --
Column 9:
Line 32, after "screen" delete "(screen)"
Line 64, after "the" (second occurrence) delete "characteristic" and insert therefor -- characteristics --
Column 11:
Line 17, after "as" insert therefor -- a --
Line 26, before "the" (first occurrence) delete "ficult on" and insert therefor -- ficult. On --
Line 34, after "screen" delete "(screen)"
Column 14:
Line 26, before "X-ray" delete "A" and insert therefor -- An --
Line 28, after "from" delete "a" and insert therefor -- an --
Line 30, after "forming" delete "a" and insert therefor -- an --
Line 31, after "by" delete "a" and insert therefor -- an --
Line 52, before "X-ray" (first occurrence) delete "a" and insert therefor -- an --

UNITED STATES PATENT AND TRADEMARK OFFICE
CERTIFICATE OF CORRECTION

PATENT NO. : 6,404,848 B1
APPLICATION NO. : 09/667009
DATED : June 11, 2002
INVENTOR(S) : Ishisaka et al.

It is certified that error appears in the above-identified patent and that said Letters Patent is hereby corrected as shown below:

Column 15:
Line 1, before "X-ray" delete "A" and insert therefor -- An --
Line 2, before "X-ray" delete "a" and insert therefor -- an --
Line 10, after "passing" insert therefor -- through --
Line 35, after "with" delete "a" and insert therefor -- an --
Column 16:
Line 18, before "X-ray" delete "A" and insert therefor -- An --
Line 19, before "X-ray" delete "a" and insert therefor -- an --
Line 23, after "passing" delete "through." and insert therefor -- through --
Line 28, after "passing" insert therefor -- through --

Signed and Sealed this

Twenty-fourth Day of July, 2007

JON W. DUDAS
*Director of the United States Patent and Trademark Office*